(12) United States Patent
Brown

(10) Patent No.: US 12,036,144 B2
(45) Date of Patent: Jul. 16, 2024

(54) SURGICAL LIMB POSITIONING AND SUPPORT DEVICE AND METHOD

(71) Applicant: Christopher James Brown, Lombard, IL (US)

(72) Inventor: Christopher James Brown, Lombard, IL (US)

( * ) Notice: Subject to any disclaimer, the term of this patent is extended or adjusted under 35 U.S.C. 154(b) by 0 days.

(21) Appl. No.: 14/726,560

(22) Filed: May 31, 2015

(65) Prior Publication Data
US 2016/0346147 A1 Dec. 1, 2016

(51) Int. Cl.
*A61G 13/00* (2006.01)
*A61F 5/37* (2006.01)
*A61G 13/12* (2006.01)

(52) U.S. Cl.
CPC ........ *A61F 5/3769* (2013.01); *A61G 13/1245* (2013.01); *A61G 13/0036* (2013.01); *A61G 2210/10* (2013.01)

(58) Field of Classification Search
CPC ........ A61F 5/37; A61F 5/3761; A61F 5/3769; A61F 5/3792; A61F 5/04; A61F 5/042; A61F 5/05; A61F 5/3707; A61F 5/05883; A61F 5/05891; A61F 2005/0139; A61F 2005/0146; A61F 2005/0151; A61F 2005/0153; A61F 2005/0155; A61G 13/10; A61G 13/12; A61G 13/1235; A61G 13/1245; A61G 13/1285; A61G 13/128; A61G 13/129; A61G 13/101; A61G 13/1205–1255; A61G 13/0036; A61G 13/0063; A61G 2200/32; A61G 7/065; A61G 7/075; A61G 7/0755; A61G 7/1096; A61G 7/109; A61G 2210/10;
(Continued)

(56) References Cited

U.S. PATENT DOCUMENTS

| | | | | |
|---|---|---|---|---|
| 541,863 A | * | 7/1895 | Loomis | A61G 13/1235 5/623 |
| 988,923 A | * | 4/1911 | Bauerfiend | A61G 13/0027 248/118 |

(Continued)

OTHER PUBLICATIONS

International Search Report mailed Oct. 26, 2016 for International Application No. PCT/US2016/034971.

*Primary Examiner* — Adam Baker
(74) *Attorney, Agent, or Firm* — McDonnell Boehnen Hulbert & Berghoff LLP

(57) ABSTRACT

A limb positioning and support device for achieving and maintaining reduction of a human bone in connection with surgical procedures involving orthopedic and other surgical fracture tables. The limb positioning and support device includes an articulating and rotating positioning and support arm coupled between a surgical table and a limb saddle. The positioning and support arm is configured to selectively allow translation and/or rotation of the limb saddle in three degrees of freedom. Actuation mechanisms drive the limb saddle vertically and horizontally. A pivot joint coupled between the limb saddle and the positioning and support arm permits rotation of the limb saddle about a vertical axis, and the limb saddle can be angularly displaced about the longitudinal axis of the subject limb. The limb saddle can be positioned and adjusted to bring fractured bone ends into alignment and hold the fracture stationary during the surgical procedure.

6 Claims, 7 Drawing Sheets

(58) Field of Classification Search
CPC ............... A61G 15/005; A61G 15/12; A61G 7/1082–1098; A61G 13/0081; A61G 13/08; A61G 13/121–1255; A61H 1/0218; A61H 1/0222; A61H 1/0237–0244; A61H 1/0274–0296
USPC .... 128/845, 846, 878, 881, 882; 5/621, 624, 5/648, 649
See application file for complete search history.

(56) References Cited

U.S. PATENT DOCUMENTS

| | | | | |
|---|---|---|---|---|
| 1,266,367 A * | 5/1918 | Wilson | ............... | A01K 87/08 248/118 |
| 1,458,933 A * | 6/1923 | Graupe | ............... | A61G 13/12 5/648 |
| 1,582,653 A * | 4/1926 | Alleyne | ............ | A61G 13/0009 5/632 |
| 1,635,638 A * | 7/1927 | Rogers | ................ | A61F 5/0193 128/882 |
| 2,020,262 A * | 11/1935 | Longfellow | ....... | A61B 17/6408 602/39 |
| 2,024,325 A | 12/1935 | Allen | | |
| 2,204,266 A * | 6/1940 | Wilcox | .............. | A61B 17/6408 5/624 |
| 2,443,106 A * | 6/1948 | Grosso | .............. | A61B 17/6408 606/56 |
| 3,596,655 A * | 8/1971 | Corcoran | ............. | A61H 1/0218 602/32 |
| 4,271,832 A | 6/1981 | Evans et al. | | |
| 4,426,071 A * | 1/1984 | Klevstad | ................ | A61G 13/12 5/602 |
| 4,475,546 A | 10/1984 | Patton | | |
| 4,807,618 A | 2/1989 | Auchinleck et al. | | |
| 4,978,348 A | 12/1990 | Ilizarov | | |
| 5,003,969 A | 4/1991 | Azer et al. | | |
| 5,162,039 A | 11/1992 | Dahners | | |
| 5,583,909 A | 12/1996 | Hanover | | |
| 5,779,249 A * | 7/1998 | Lin | ...................... | B62K 19/36 280/287 |
| 5,806,117 A | 9/1998 | Gotfried | | |
| 6,154,901 A * | 12/2000 | Carr | ...................... | A61G 13/12 5/601 |
| 6,467,487 B1 * | 10/2002 | Rios | ...................... | A61F 5/3761 128/869 |
| 8,302,228 B2 | 11/2012 | Aboujaoude | | |
| 2003/0114780 A1 * | 6/2003 | Al-Obaidi | ............ | A61H 1/0296 601/39 |
| 2004/0003468 A1 * | 1/2004 | Mitsuishi | ............. | A61H 1/0255 5/624 |
| 2007/0251011 A1 | 11/2007 | Matta et al. | | |
| 2010/0263129 A1 | 10/2010 | Aboujaoude | | |
| 2012/0103344 A1 * | 5/2012 | Hunter, Jr. | ............ | A61F 5/3761 128/845 |
| 2012/0233782 A1 * | 9/2012 | Kreuzer | ............... | A61G 13/125 5/624 |
| 2014/0068863 A1 | 3/2014 | Clark et al. | | |
| 2014/0115786 A1 * | 5/2014 | Wilson | ................ | A61G 13/121 5/622 |
| 2014/0208514 A1 | 7/2014 | Schuerch, Jr. | | |
| 2014/0364785 A1 * | 12/2014 | Moore | ............... | A61F 5/0193 602/19 |

* cited by examiner

SURGICAL LIMB POSITIONING AND SUPPORT DEVICE AND METHOD

FIELD

This disclosure relates to orthopedic surgery, and more particularly to devices, systems, and methods for treating fractures and correcting malunions and non-unions of long bones. Specifically, but not exclusively, the disclosure relates to achieving and maintaining reduction of a human femur in connection with antegrade intramedullary nail fixation, cephalomedullary nail fixation, and open reduction internal fixation involving orthopedic and other surgical fracture tables.

BACKGROUND

Intramedullary fixation systems and, in particular, intramedullary femoral nails or rods, are commonly used in the treatment of fractures, such as those resulting from traumatic injuries, malunions, and non-unions of long bones. In surgical procedures involving femoral fractures, malunions, and non-unions, it is essential that fractured bone segments be properly positioned and aligned prior to intramedullary fixation. Fracture reduction is typically achieved by the positioning of the patient, manual external manipulation of the limb by the surgeon or other medical professional, open reduction internal fixation (ORIF), fraction, or a combination of one or more of these methods.

A common femoral intramedullary fixation procedure involves the use of a fracture table, such as the fracture table described in U.S. Patent Application Publication No. 2007/0251011 to Matta, et al. In a typical fracture table application, a patient is supported on a platform portion of the fracture table in the supine position generally parallel to the operating room floor. Two elongated cantilever spars extend from the platform portion of the table distally, generally parallel and posterior to the patient's legs. A traction system disposed at the distal end of each spar engages the distal portion of the patient's corresponding leg (or foot). The traction systems may be manipulated to apply a desired amount of traction or compression along the longitudinal axis of each leg. The spars are adjustable to maneuver the patient's legs into a desired position for surgery. Fracture tables also generally include systems for adjusting other portions of the patient, such as the patient's hips. The portion of the patient's fractured leg between the hip and lower leg is not supported. This state provides virtually unobstructed access to the surgical area, and enables liberal adjustment of the fractured ends of the bone segments relative to each other.

While the patient is mounted on the fracture table, reduction of the fracture is typically achieved by a combination of adjustment of the traction force provided by the corresponding traction system, manual alignment and positioning of the limb by the surgeon or other medical professional, and adjustment of the patient's position with the aid of adjustable portions of the fracture table. Relative positioning of the fractured bone ends is achieved along the longitudinal axis of the subject leg by adjusting the traction applied by the traction systems, and relative rotational orientation about the longitudinal axis is achieved by rotational adjustment of a portion of the fracture table. However, relative positioning in planes orthogonal to the longitudinal axis, and rotation about axes orthogonal to the longitudinal axis, are typically achieved by manual external manipulation or internal manipulation and reduction with the aid of bone clamps.

Although manual manipulation can be successfully employed to reduce the fracture, the process is time-consuming and highly susceptible to human error. Because the fractured or affected limb is typically suspended between the hip and lower leg, gravitational forces can cause posterior displacement or sagging of the fracture. Muscle tension and other forces internal to the limb also may act to misalign the fractured bone ends. Achieving and maintaining full reduction generally requires that the limb be supported at an intermediate position to counteract the gravitational and internal forces, and to align and maintain alignment of the fractured bone ends. Even after achieving reduction by manual manipulation, it is impractical or even impossible for the surgeon or other medical professional to manually hold the limb in the reduced position until the fractured bone segments are surgically secured.

Accordingly, devices and methods have been developed or improvised to position and hold the fractured bone ends in alignment. For example, a common method employs a standard medical crutch as a columnar support between the limb and the operating room floor. In this method, the surgeon can align the fractured bone ends by adjusting the position of the crutch and its angle relative to the operating room floor. Although this method does not require expensive and specialized equipment, it is deficient because, among other things, precise positioning of the crutch is difficult and often requires several iterative adjustments to achieve fracture reduction. The adjustment process is time-consuming, imprecise, and discourages the application of fine adjustments to achieve a nominally reduced fracture. Additionally, because fracture reduction is typically achieved while the crutch is non-perpendicular to the operating room floor, the method relies on friction between the crutch and the operating room floor, as well as between the crutch and the limb, to maintain the reduced position and hold the crutch in place. Slippage of the crutch is common and typically results in misalignment of the fractured bone ends. Also, adjusting the traction applied to the affected limb while the crutch is installed can lead to slippage or anterior or posterior displacement and misalignment of the fractured bone ends. Furthermore, the crutch is at risk of being misaligned or dislodged by accidental contact with medical personnel or surgical or other medical equipment.

To assist the surgeon and other medical professionals in reducing the fracture, a C-arm x-ray imaging system, such as the system described in U.S. Pat. No. 5,583,909 to Hanover, is typically employed to provide visual indication of the relative position and orientation of the bone segments before, during, and after reduction of the fracture, as well as throughout the surgical procedure to verify proper alignment of the bone segments. Because x-ray images are two-dimensional projections, determination of the relative position and orientation of the bone segments in each of the six degrees of freedom requires x-ray images in at least two different projection planes.

It is desirable to accommodate unrestricted positioning and movement of the C-arm x-ray imaging system about the fractured or affected limb. Fracture tables are typically configured to minimize obstruction about the fractured or affected limb, thereby providing extensive access to limb by the surgeon and x-ray or other imaging systems. The crutch employed in the method described above restricts the positioning and freedom of movement of the C-arm x-ray imaging system, thus requiring cumbersome and time-consuming maneuvering around the crutch.

Moreover, after reduction of the fracture and prior to invasive surgery, a sterile field is established around the surgical site. Sterilization of the surgical site requires unobstructed access to the exterior surface of the limb for wiping, application of sterilizing fluids, and draping. Accordingly, any intermediate support of the limb within the surgical site or sterile filed must be removed prior to invasive surgery to permit sterilization of the limb and establishment of the sterile field. In the crutch method described above, the position of the crutch when the fracture is fully reduced is typically recorded by placing adhesive tape or otherwise marking the location where the crutch contacts the operating room floor. Generally, because the surface of the limb must be sterilized, the location at which the crutch engages the fractured or affected limb cannot be marked directly on the limb. After sterilization, although the surgeon and/or assistants can generally return the crutch to a position that approximates the position of the crutch in the fully reduced state, the imprecision inherent in the method often necessitates additional adjustment of the crutch and/or the fracture table to return the fracture to the fully reduced state prior to invasive surgery. It is therefore desirable to provide a limb positioning and support device and method for quickly, easily, safely, and precisely assisting with positioning and alignment of fractured bone ends, disengaging the limb support from the fractured limb during sterilization and preparation for invasive surgery, and returning the limb positioning and support device to a predetermined position with precision.

SUMMARY

An object of the present disclosure is to provide a limb positioning and support device that is easily adjusted to position fractured bone segments of a fractured femur or other long bone into a fully reduced state, and that can precisely maintain the limb in the reduced state throughout a surgical procedure.

In various operations and medical procedures fractured ends of fractured bone segments must be located and adjusted precisely, and held stationary during the operation or procedure. For example, antegrade intramedullary nail fixation, cephalomedullary nail fixation, and open reduction internal fixation procedures typically involve the use of orthopedic and other surgical fracture tables to apply traction to the fractured or affected limb, and to adjust the rotational alignment of fractured bone ends about the longitudinal axis of the limb. However, it is also desirable to align the fractured ends of fractured bone segments in a plane perpendicular to the longitudinal axis of the limb in order to achieve reduction of the fracture. The fracture also must be held in the reduced state during the surgical procedure. Alignment is critical and minute adjustments may be required.

The present application achieves these desired results through a limb positioning and support device that includes an articulating and rotating positioning and support arm coupled between a surgical table and a limb saddle. The limb positioning and support device is rigidly securable to the surgical table via an accessory rail mounting clamp or rail mount. The positioning and support arm is configured to selectively allow translation and/or rotation of the limb saddle in three degrees of freedom. An actuation mechanism is configured to drive the limb saddle vertically (i.e., along an anterior-posterior axis of a patient supported on the operating table in the supine position), and a second actuation mechanism is configured to drive the limb saddle horizontally (e.g., along the lateral-medial or superior-inferior axes). A pivot joint coupled between the limb saddle and the positioning and support arm permits rotation of the limb saddle about a vertical axis, and the limb saddle may be angularly displaced about the longitudinal axis of the subject limb.

Once a patient is mounted on the operating table and traction is applied to the fractured or affected limb, the limb saddle may be positioned and adjusted to engage the posterior of the limb and drive one or more fractured bone ends into vertical alignment. The limb saddle may also be positioned to simultaneously engage either the medial or lateral side of the limb and drive one or more fractured bone ends into horizontal alignment. Once the fracture is fully reduced, the limb positioning and support device, in conjunction with the surgical table, holds the fracture stationary during the surgical procedure.

The present inventive subject matter also provides a limb positioning and support device that can disengage from the fractured or affected limb after the fracture has been reduced, to permit sterilization and draping of the limb in preparation for invasive surgery, and thereafter may be easily and precisely returned to the position at which reduction of the fracture was achieved. This allows for the surgeon to reduce the fracture prior to the establishment of a sterile field, yet allows the surgeon to quickly, reliably, and precisely return the fracture to the reduced state after the fracture has been unsupported during sterilization and preparation for invasive surgery.

Additional objectives of the present inventive subject matter are to provide a limb positioning and support system that is easy to use, sturdy, reliable, radiolucent, easily mounted and dismounted from a surgical table, easily cleaned and sterilized if desired, and is configured to maximize access to the surgical site and provide for unimpeded positioning and movement of x-ray imaging equipment, such as a C-arm x-ray imaging device, about the subject fracture and surgical site.

These and other embodiments are described in more detail in the following detailed descriptions and the figures. The foregoing is not intended to be an exhaustive list of embodiments and features of the present inventive subject matter. Persons skilled in the art will appreciate other embodiments and features from the following detailed description in conjunction with the drawings.

BRIEF DESCRIPTION OF THE DRAWINGS

Embodiments of the present disclosure are described by way of following drawings pointing out the various details of the device and method of the present inventive subject matter. The main features and advantages of the present disclosure will be better understood with the following descriptions, claims, and drawings, where:

DETAILED DESCRIPTION

Figure 1:
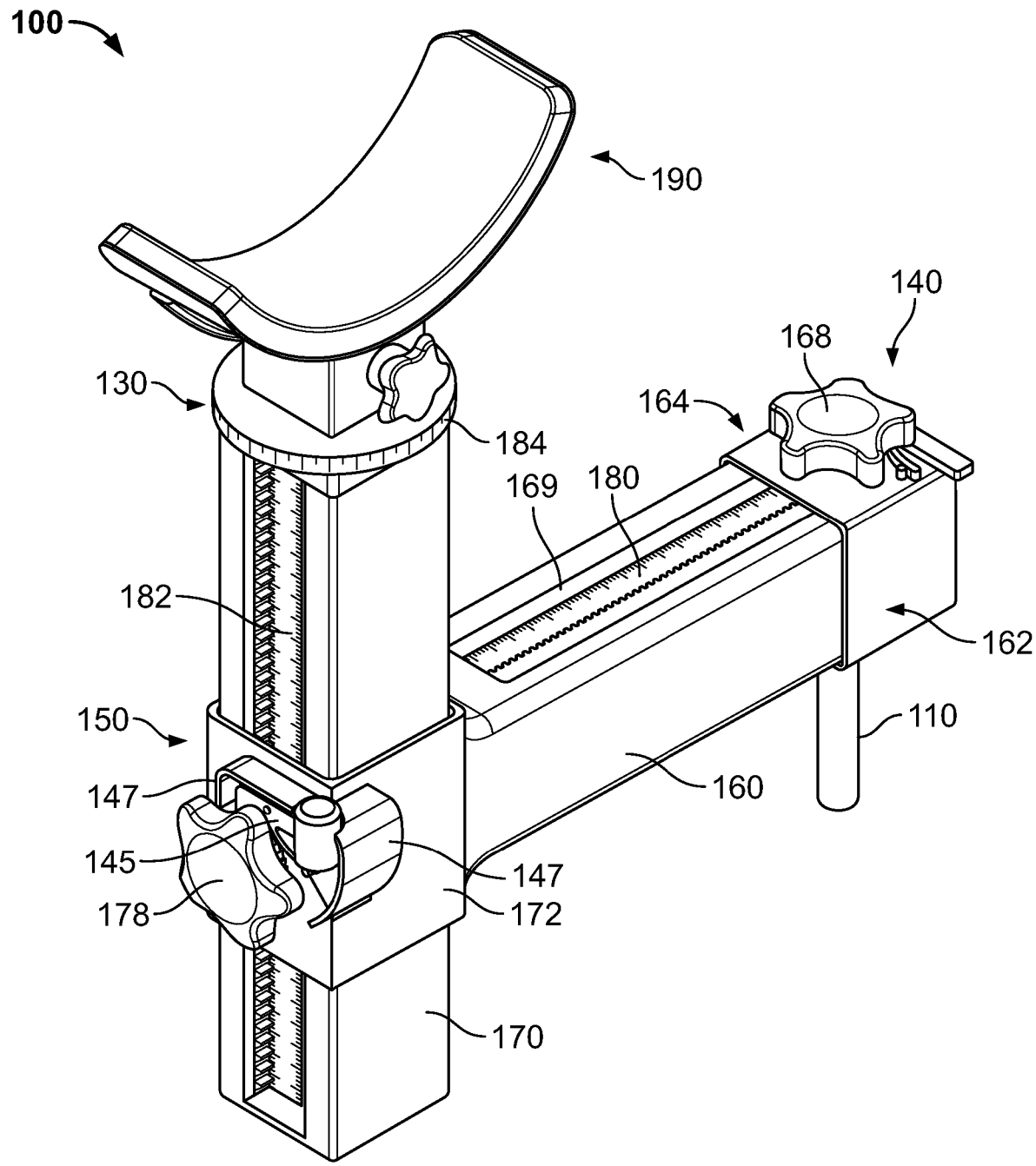
FIG. 1 is a diagram illustrating an isometric view of a limb positioning and support device in accordance with an embodiment of the devices and methods described herein.

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details.

Various aspects of a limb positioning and support device may be illustrated by describing components that are connected, coupled, attached, and/or joined together. As used herein, the terms "connected", "coupled", "attached", and/or "joined" are used interchangeably to indicate either a direct connection between two components or, where appropriate, an indirect connection to one another through intervening or intermediate components.

Relative terms such as "lower" or "bottom", "upper" or "top", and "vertical" or "horizontal" may be used herein to describe one element's relationship to another element illustrated in the drawings. It will be understood that relative terms are intended to encompass different orientations of a limb positioning and support device in addition to the orientation depicted in the drawings. By way of example, if aspects of a limb positioning and support device shown in the drawings are turned over, elements described as being on the "bottom" side of the other element would then be oriented on the "top" side of the other elements as shown in the relevant drawing. The term "bottom" can therefore encompass both an orientation of "bottom" and "top" depending on the particular orientation of the drawing.

Reference will now be made to figures wherein like structures are provided with like reference designations. It should be understood that the figures are diagrammatic and schematic representations of exemplary embodiments of the invention of the present disclosure, and are neither limiting nor necessarily drawn to scale.

One embodiment of the limb positioning and support device of the present disclosure is illustrated in FIGS. 1-5b, and is generally indicated as limb positioning and support device 100. In this embodiment, the limb positioning and support device 100 includes a mounting device 110 and a limb saddle 190.

Connected between the mounting device 110 and the limb saddle 190 is a positioning and support arm 150. The positioning and support arm 150 includes a horizontal member 160 extending along a horizontal axis and a vertical member 170 extending along a vertical axis. To aid in understanding of the devices and methods of the present disclosure, reference will be made to a Cartesian coordinate system. In this embodiment, the horizontal axis corresponds to an X-axis, and the vertical axis corresponds to a Y-axis of the Cartesian coordinate system. A first prismatic joint 162, coupled between the mounting device 110 and the horizontal member 160, permits linear displacement of the horizontal member 160 relative to the mounting device 110 along the X-axis. A second prismatic joint 172, coupled between the horizontal member 160 and the vertical member 170, permits linear displacement of the vertical member 170 relative to the horizontal member 160 along the Y-axis. A pivot joint 130, coupled between the vertical member 170 and the limb saddle 190, permits rotation of the limb saddle 190 about the vertical Y-axis. In this configuration, the positioning and support arm 150 allows for manipulation of the limb saddle 190 in at least three degrees of freedom relative to the mounting device 110.

Figure 2:
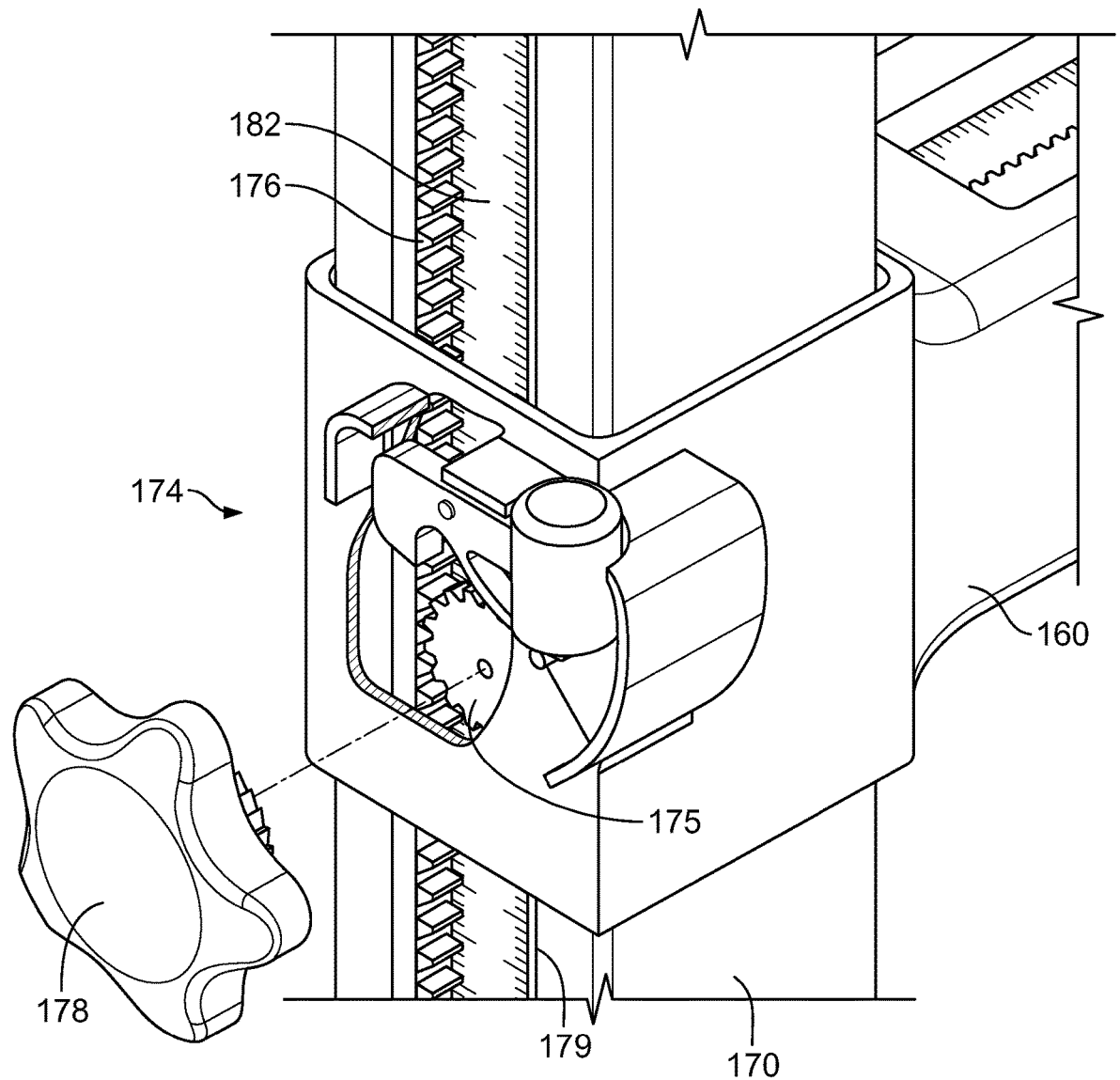
FIG. 2 is an isometric detail diagram, in partial section, illustrating a portion of a limb positioning and support device in accordance with an embodiment of the devices and methods described herein.

Linear displacement of the vertical member 170 along the Y-axis relative to the mounting device 110 may be driven by an actuation mechanism 174. In this embodiment, as illustrated in FIG. 2, the actuation mechanism 174 includes a rack gear 176 disposed in a recessed channel 179 running along the longitudinal axis of the vertical member 170, and a pinion gear 175 pivotally connected to a distal end of the horizontal member 160 and arranged to engage the rack gear 176. Manual rotation of a vertical control knob 178, which is connected to the pinion gear 175, causes linear displacement of the vertical member 170 along the Y-axis. Displacement of the horizontal member 160 along its longitudinal axis and relative to the mounting device 110 is accomplished by a second actuation mechanism 164 that is similar in structure and operation to the actuation mechanism 174 of the vertical member 170. The second actuation mechanism 164 includes a horizontal control knob 168, a second pinion gear 165, and a second rack gear 166 that runs in a second recessed channel 169 along the longitudinal axis of the horizontal member 160. Manual rotation of the horizontal control knob 168 causes linear displacement of the horizontal member 160, and consequently the limb saddle 190, along the X-axis.

Although prismatic joints, rack and pinion gears, and manual control knobs are discussed, it should be recognized that support and positioning of the limb saddle may be accomplished with a variety of devices or apparatuses that will be appreciated by one of ordinary skill in the art. For example, without limitation, the limb positioning and support device may include one or more telescoping mechanisms, rod-and-cylinder or piston mechanisms, Hoekens linkages, Peaucellier-Lipkin linkages, and other slot-type linkages. By way of further example, linear or quasi-linear roller bearings may be employed to permit motion of one or more components in one or more degrees of freedom, while constraining motion in another one or more degrees of freedom. Preferably, the limb positioning and support device provides for adjustment of the limb saddle in each degree of freedom independently. Linear displacement of the limb saddle may be accomplished by any appropriate device or apparatus known or used in the art for imparting a controlled amount of linear or quasi-linear displacement. For example, without limitation, the limb positioning and support device may include one or more mechanical, electro-mechanical, hydraulic, electro-hydraulic, pneumatic, electro-pneumatic, or electro-magnetic linear actuators that may include one or more gears, levers, power screws, ACME screws, ball screws, pistons, belts, cables, chains, pressure chambers, and electro-magnetic devices to achieve linear displacement of the limb saddle relative to the mounting device. Preferably, actuation of the limb saddle in each degree of freedom may be accomplished independent of actuation in the other degrees of freedom. Linear displacement may be powered manually or by an internal or external power source, such as an electric battery, power line connection, or hydraulic or pneumatic lines. In some embodiments, the linear actuation device includes a plurality of selectable input to output ratios for varying the displacement length per unit of input. For example, the actuation mechanism in one embodiment is configured to be selectable between a low gear ratio and a high gear ratio. The low gear ratio provides for finer adjustment, greater control, and higher driving force than the high gear ratio, which allows for faster positional adjustments as desired, such as when the limb saddle is disengaged from the limb. In some embodiments, the actuation mechanism includes a gearbox, planetary gearhead, or similar arrangements of multiple gears to achieve various displacement lengths per unit of input. In some embodiments, linear displacement may be controlled manually, and in other embodiments control may be automated based on manual input.

Figure 3:
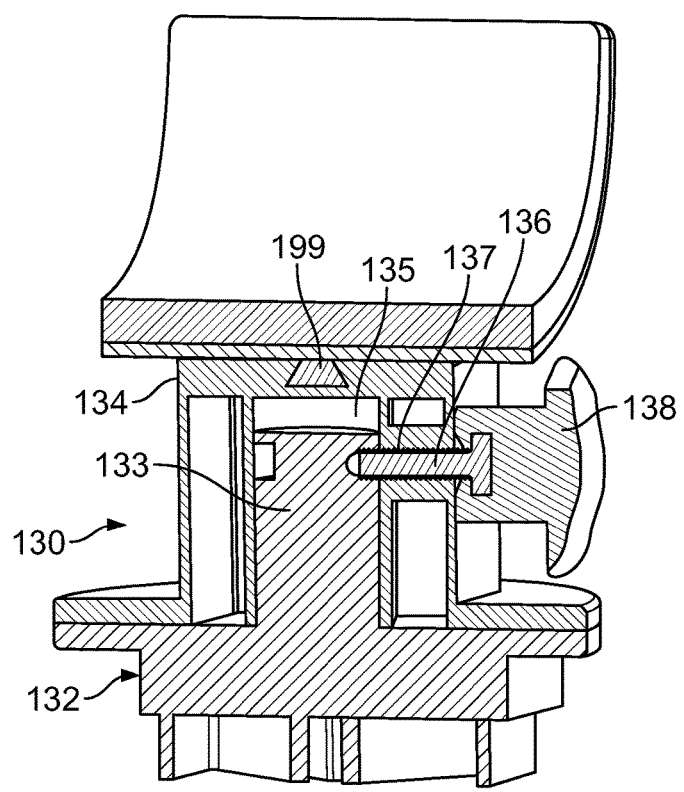
FIG. 3 is a section view diagram illustrating a portion of a limb positioning and support device in accordance with an embodiment of the devices and methods described herein.

Referring again to the limb positioning and support device 100 of FIGS. 1-5b, as illustrated in FIG. 3, connected at the upper end of the vertical member 170 is a pivot joint 130, which includes a base plate 132, connected to the vertical member 170, and a pivot plate 134. The base plate 132 includes a vertically extending cylindrical post 133, and pivot plate 134 includes a cylindrical bore 135 configured to receive the vertically extending cylindrical post 133, permitting rotation of the pivot plate relative to the base plate about the vertical or Y-axis. A set screw 136 extends through a threaded bore 137 in the pivot plate 134 and may be tightened against the vertically extending post 133 to releasably secure the position and orientation of the base plate relative to the pivot plate. The set screw 136 is fitted with a knob 138 for easy manipulation by a medical professional.

Figure 4:
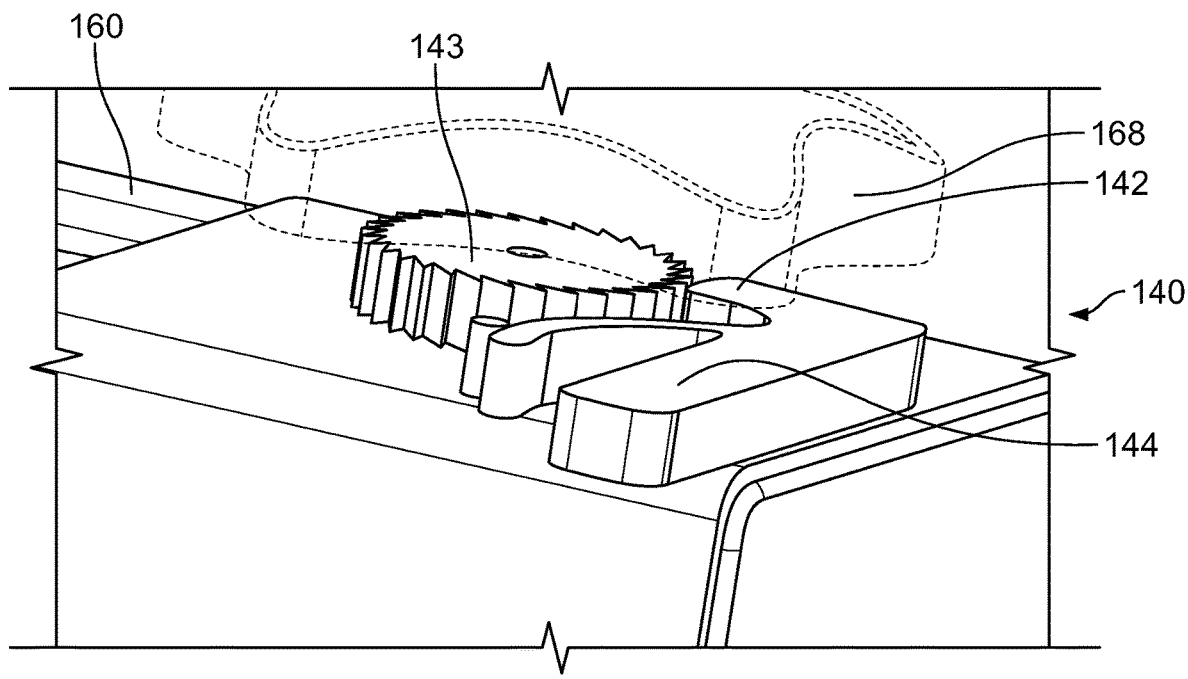
FIG. 4 is an isometric detail view diagram, in partial phantom, illustrating a portion of a limb positioning and support device in accordance with an embodiment of the devices and methods described herein.
Figure 5A:
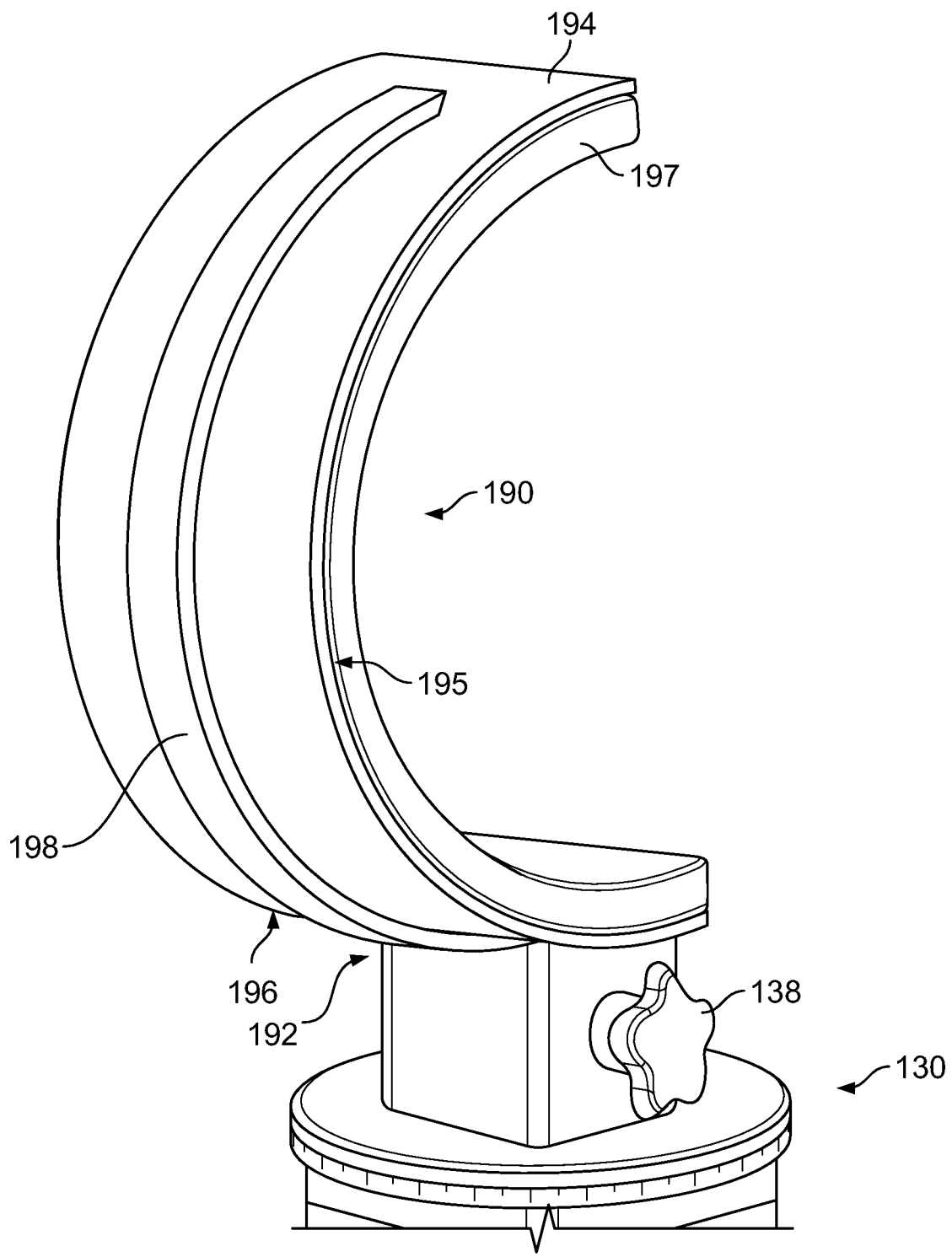
FIG. 5a is an isometric detail view diagram, in partial section, illustrating a limb positioning and support device in accordance with an embodiment of the devices and methods described herein, wherein a limb cradle of such device is illustrated in a first position.
Figure 5B:
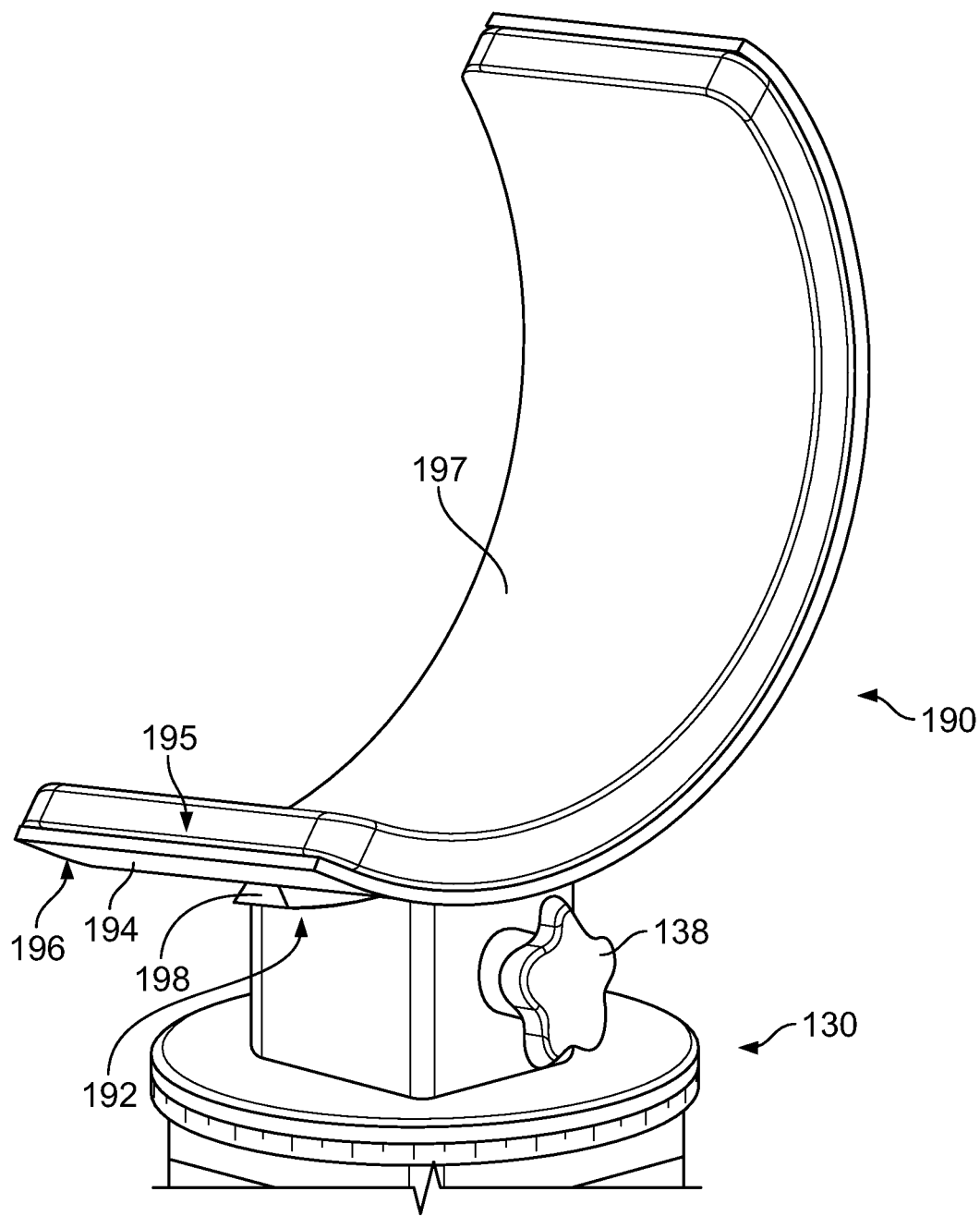
FIG. 5b is an isometric detail view diagram, in partial section, illustrating a limb positioning and support device in accordance with an embodiment of the devices and methods described herein, wherein a limb cradle of such device is illustrated in a second position.
Figure 6:
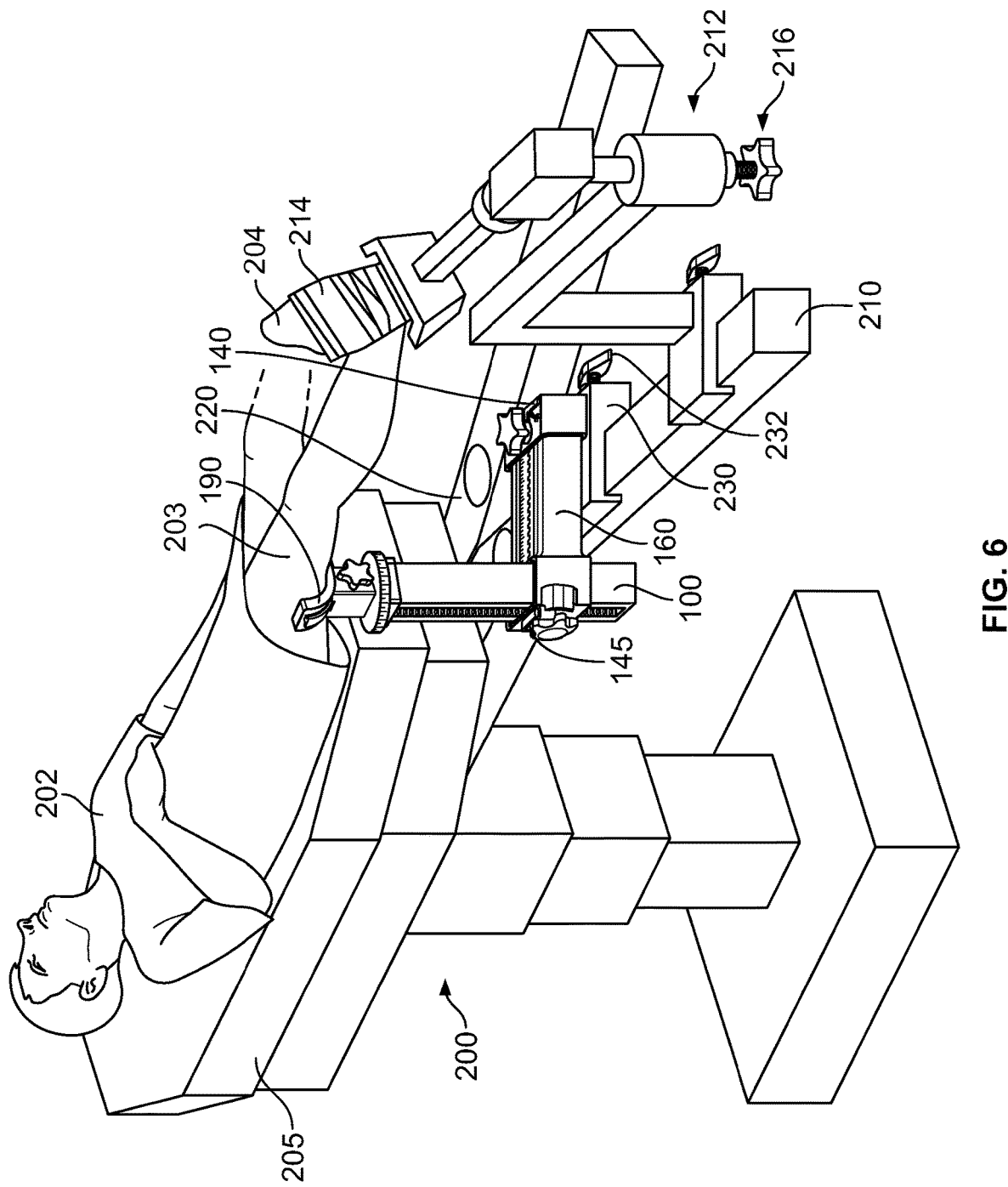
FIG. 6 is an isometric diagram illustrating a perspective view of a limb positioning and support device in accordance with an embodiment of the devices and methods described herein, illustrated with a patient in a supine position supported by a conventional fracture table partially depicted.

Referring to FIGS. 5a-5b, the limb saddle 190 includes a limb saddle plate 194, and a limb receiving pad 197. In the embodiment illustrated in FIGS. 1-5b, the limb receiving plate 194 is C-shaped, having a concave inner surface 195 and a convex outer surface 196. A mounting ridge 198, dovetail-shaped in transverse cross-section, extends annularly along the convex outer surface 196. The mounting ridge 198 is inserted into a mating channel 199, dovetail-shaped in transverse cross-section, formed in the pivot plate 134 of the pivot joint 130, thus providing a sliding joint 192 that permits orbital rotation of the limb saddle 190 about a central axis of an abstract cylinder (not shown) having a surface that is co-extensive with the concave inner surface 195. Alternatively stated, the central axis coincides with the center of curvature of the concave inner surface 195. Although the inner surface 195, outer surface 196, mounting ridge 198, and mating channel 199 preferably each have a uniformly circular C-shape, it should be appreciated that one or more of these members may alternatively comprise other arcuate forms As described more fully below, during a typical surgical procedure involving the limb positioning and support device 100, the central axis will be generally aligned with a longitudinal axis of a patient's fractured or affected limb 203, as illustrated in FIG. 6. As illustrated in FIG. 5a, the limb saddle 190 is shown in a first orientation generally to the left side of the central longitudinal axis of the vertical member 170. The sliding joint 192 permits the limb saddle 190 to be orbitally rotated about the central axis to a second orientation generally to the right side of the longitudinal axis of the vertical member 170, as illustrated in FIG. 5b. It should be appreciated that in addition to the orientations illustrated in FIGS. 5a-5b, the limb saddle 190 may be oriented in a variety of orbital positions including, without limitation, a position in which the limb saddle is equally distributed on either side of the longitudinal axis of the vertical member, as illustrated in FIGS. 1-4. In some embodiments, a set screw or other locking mechanism is included to secure the sliding joint 192 and prevent orbital rotation of the limb saddle 190 about the central axis. The cross-section of the mounting ridge 198 may be dovetail-shaped, T-shaped, or have any other shape suitable for slidably coupling the limb saddle 190 to the pivot plate 134. Alternatively, the outer surface 196 may be slidably coupled to the pivot plate 134 via any suitable means for allowing orbital rotation, including, without limitation, curvilinear roller bearings, track and wheel mechanisms, and pivoting and/or sliding linkages. The inner surface 195 of the limb saddle 190 is padded for the patient's comfort with a limb receiving pad 197. In some embodiments, the limb receiving pad is removable for easy cleaning and sterilization. Preferably, the limb receiving pad is inexpensively manufactured such that the limb receiving pad is intended for single-use and is disposable.

In some embodiments, the limb positioning and support device includes an actuation mechanism configured to drive rotation of the limb saddle about the Y-axis. In some embodiments, an actuation mechanism is included to drive angular displacement of the limb saddle about the central longitudinal axis. It should be recognized that a variety of known devices and apparatuses would be suitable for driving, controlling, and securing rotation of the limb saddle about the Y-axis and about the central longitudinal axis. For example, without limitation, one or more worm gear mechanisms may be configured to drive rotation of the limb saddle by manipulation of a control knob or by motorized control.

Referring now to FIG. 4, the limb positioning and support device 100 of the embodiment of FIG. 1 includes a releasable locking device 140 to selectively lock the position of the horizontal member 160 along the X-axis. In this embodiment, the locking device 140 is spring-biased toward an engaged state in which ramped teeth of a pawl 142 engage teeth of the ratchet gear 143. In this state, rotation of the pinion gear is permitted in one direction, but rotation in the opposite direction is prevented, thereby permitting positive ratcheting displacement of the horizontal member along the X-axis and preventing negative displacement. A release lever 144 is provided for manually disengaging the pawl 142 from the ratchet gear 143, thereby permitting free rotation of the ratchet gear and displacement of the horizontal member 160 along the X-axis in both the positive and negative directions. A second releasable locking device 145 is provided to selectively lock the position of the vertical member 170 along the Y-axis. In this embodiment, as illustrated in FIGS. 1-2, a release shield 147 is provided near the release lever or button of the locking device 145 to reduce the risk of accidental disengagement of the locking device 145. The locking devices 140, 145 may be provided with a variety of shields, covers, levers, locks, or other safety devices that are well known in the art for preventing accidental manipulation of levers, buttons, and similar devices.

In one alternative embodiment, the locking device is spring-biased toward a fully locked state that prevents rotation of the pinion gear in both directions. In other embodiments, the locking device is not spring-biased, thus requiring manual input to switch between engaged and disengaged states. In other embodiments, the locking device includes an engaged ratcheting state that permits positive rotation of the pinion gear while preventing negative rotation, and a second engaged ratcheting state that prevents positive rotation while permitting negative rotation. In another embodiment, the locking device includes a fully unlocked state, one or more ratcheting states, and a fully locked state. In another embodiment, the locking device is selectable between spring-biased and fully manual switching modes. In other embodiments, the locking device includes one or more variations or combinations of the above-described embodiments.

As illustrated in FIG. 1, visual indicators 180, 182, 184 are provided to aid in determining the position and orientation of the limb saddle 190 relative to the mounting device 110. Although visual indicators 180, 182, 184 are illustrated as linear or angular scale markings, it should be understood that positional indication may be accomplished with numerous suitable indicia and devices. For example, without limitation, position may be measured with geared or threaded mechanisms, rotary and linear transducers, Hall effect sensors, potentiometers, optical sensors, accelerometers, or laser, radar or sonic measurement devices. The measured position may be visually displayed by a mechanical indicator or by analog or digital electrical displays, such as an LED display. Alternatively, the measured position may be indicated audibly or stored in an electronic memory device. In one embodiment, the limb positioning and support device includes one or more moveable markers that can indicate a desired position, such as the position of the limb saddle in the fully reduced position, even when the limb saddle is displaced from the marked position. This has the advantage of assisting the surgeon in accurately returning the limb saddle to the marked position. In another embodiment, the limb positioning and support device includes one or more adjustable hard stop devices, such as a collar clamp tightened via compression screw or set screw. These adjustable hard stop devices may be positioned to limit undesired displacement of the limb saddle beyond a predetermined position. In some embodiments, it is desirable to provide force measurement devices, such as linear force transducers or strain gauges to measure and/or limit force applied to the fractured or affected limb.

The limb positioning and support device of the present disclosure has a preferred method of operation as described below. It will be appreciated that the methodology used will vary depending on the medical professional and the surgical procedure. Additionally, standard operating procedures may be used, but are not necessarily described herein, such as the use of gauze and sterilization procedures. As used herein, the term surgeon may include other medical professionals or any other person or device without limiting the scope of the devices and methods of the present disclosure.

In one preferred method of operation, the limb positioning and support device 100 is used to assist a surgeon in reducing a femoral fracture and holding the fracture in a reduced state during a femoral intramedullary fixation procedure. Referring to FIG. 6, a patient 202 is supported in a supine position on an operating table, illustrated as fracture table 200. The patient's torso is supported by a patient support base 205. Leg support beams 210, 220 extend from the patient support base 205 generally below and parallel to the longitudinal axis of each respective leg of the patient. The leg support beam 210 has a traction system 212. A fraction boot 214 is employed for receiving a foot 204 of the patient and holding the foot 204 in a desired position. A fraction adjustment mechanism 216 may be adjusted to apply a desired amount of traction to the patient's limb 203.

The limb positioning and support device 100 is mounted to a standardized accessory mount 230 that is secured to the leg support beam 210 corresponding to the fractured or affected limb 203 of the patient. In this embodiment, the accessory mount 230 is illustrated as a Clark attachment, and the mounting device 110 includes a solid metal Clark post adapted to be received by the Clark attachment and releasably secured by a clamping mechanism 232 of the accessory mount 230. The limb positioning and support device 100 may be mounted in a variety of orientations to accommodate varied operating tables and patient positions. In this illustrated embodiment, the limb positioning and support device 100 is mounted such that the horizontal member 160 extends laterally outward from the patient's midsagittal plane. It should be noted that, in this embodiment, the X-axis of the limb positioning and support device 100 extends generally from the patient's left to right, the Y-axis extends generally from the patient's anterior to posterior (i.e., front to back), and the Z-axis extends generally from the patient's superior to inferior portions (i.e., head to toe). Alternatively, the limb positioning and support device may be mounted such that the horizontal member 160 extends along the Z-axis, or at any oblique angle, to accommodate fracture table configurations wherein the leg support beam is positioned directly below the patient's limb 203. In this configuration, rotation of the limb saddle 190 about the Y-axis may align the limb saddle for proper engagement with the limb 203.

To achieve reduction of the fracture, the surgeon, aided by x-ray images, adjusts the fracture table 200 to apply an appropriate amount of traction to the affected limb 203, and to align the fractured bone ends by relative rotation about the longitudinal axis of the affected limb 203. The surgeon determines an appropriate location for the limb saddle 190 to engage the limb 203 to avoid intrusion into the surgical site and to provide appropriate support to achieve and maintain fracture reduction. The limb saddle 190 is pivoted to orient the central longitudinal axis generally parallel to the longitudinal axis of the affected limb 203 as shown in FIG. 6. The surgeon adjusts the position of the limb saddle 190 to engage the limb and drive the fractured bone ends into alignment. Adjustment of the limb saddle 190 to a desired position along the longitudinal axis of the affected limb (i.e., the Z-axis) is accomplished by adjusting the position of the accessory mount 230 along the length of the leg support beam 210. The position of the limb saddle 190 along the X-axis is adjusted by rotating the horizontal control knob 168 or applying a force to the horizontal member 160 along the X-axis. In this embodiment, the locking device 140 must be disengaged in order to move the limb saddle 190 horizontally toward the mounting device 110. The position of the limb saddle 190 along the Y-axis is similarly adjusted by rotating the vertical control knob 178 or by manually applying force along the Y-axis of the vertical member 170. In this embodiment, the locking device 145 must be disengaged in order to move the limb saddle 190 vertically downward.

The limb saddle 190 may be positioned to engage any of the medial, lateral, and posterior portions of the fractured or affected limb 203. This is particularly advantageous where the surgeon desires to adjust the fracture ends of the fractured bone segments in either of the medial or lateral directions. The limb saddle 190 may be adjusted by rotating it about the Y-axis. However, it should be noted that, while the limb saddle 190 is positioned adjacent to the patient's limb 203, larger rotations about the Y-axis would require the limb saddle 190 to be lowered to avoid interference from the limb 203 during rotation. Alternatively, the surgeon may orbitally rotate the limb saddle 190 to any of the medial, lateral, or posterior portions of the limb 203 by sliding the mounting ridge 198 through the mounting channel 199. Such adjustment can be made without lowering the entirety of the limb saddle 190 below the limb 203.

Aided by x-ray images, the surgeon adjusts the position of the limb saddle 190 to engage and manipulate the fractured or affected limb 203 in at least two degrees of freedom to align the fractured bone ends. Additional adjustments may be made by manipulating the fracture table 200 to increase or reduce the applied traction and rotate the fractured bone segments about the longitudinal axis of the limb 203. When complete reduction of the fracture is achieved, the limb positioning and support device 100, in conjunction with the positioning and traction mechanisms of the fracture table 200, restrict relative displacement of the fractured bone ends, thus holding the fracture in the reduced state.

After the fracture is reduced, it is desirable to provide unobstructed access to the exterior surface of the limb 203 for wiping, application of sterilizing fluids, and draping prior to invasive surgery. Because disengaging the limb saddle 190 from the limb may cause the fracture to fall out of the reduced state, the surgeon records the position of the limb saddle 190 in the reduced state by referring to the visual position indicators 180, 182, 184 prior to disengaging the limb saddle 190. The surgeon lowers the limb saddle 190 by disengaging the locking device 145 and either rotating the vertical control knob 178 or manually applying downward force along the Y-axis of the vertical member 170 to disengage and lower the limb saddle 190 away from the limb 203. The surgeon may similarly manipulate the horizontal position of the limb saddle 190 as necessary. When the limb saddle 190 is disengaged from the limb 203, a sterile barrier (e.g., a surgical drape) (not shown) may be established between the limb and the limb positioning and support device 100 such that the limb positioning and support device 100 is located outside of a sterile field established around the surgical site. After the sterile field is established, the surgeon or other medical professional manipulates control knobs 168, 178 to return the limb saddle 190 to the reduced state position. By referring to visual position indicators 180, 182, 184 the limb saddle 190 may be returned to the reduced state position with high accuracy, typically returning the fracture to the reduced state with little or no additional adjustment required. If necessary, the surgeon may make additional adjustments from within the sterile field by manipulating the sterile side of the surgical drape or other sterile barrier to access the control knobs 169, 178. Alternatively, the surgeon can direct an assistant to make adjustments from outside of the sterile field.

In various alternative embodiments, positioning of the limb saddle is actuated with the aid of electric motors or other powered devices. In the embodiment illustrated in FIG. 7, the limb positioning and support device 300 includes telescoping members 380, 382 actuated via internal power screws (not shown) that are driven by rotary electric motors 392, 394 controlled by a control module 310. The control module 310 is configured to receive an input corresponding to a desired position and subsequently control the actuation devices to achieve the desired position. Such configuration would advantageously allow for precise control of certain parameters such as the rate of motion. The power screws are non-backdriveable and able to hold the limb saddle 390 stationary—even when external force is applied to the limb saddle 390—without the need for locking mechanisms. Manual control knobs 368, 378 can be included to allow manual adjustments.

Figure 7:
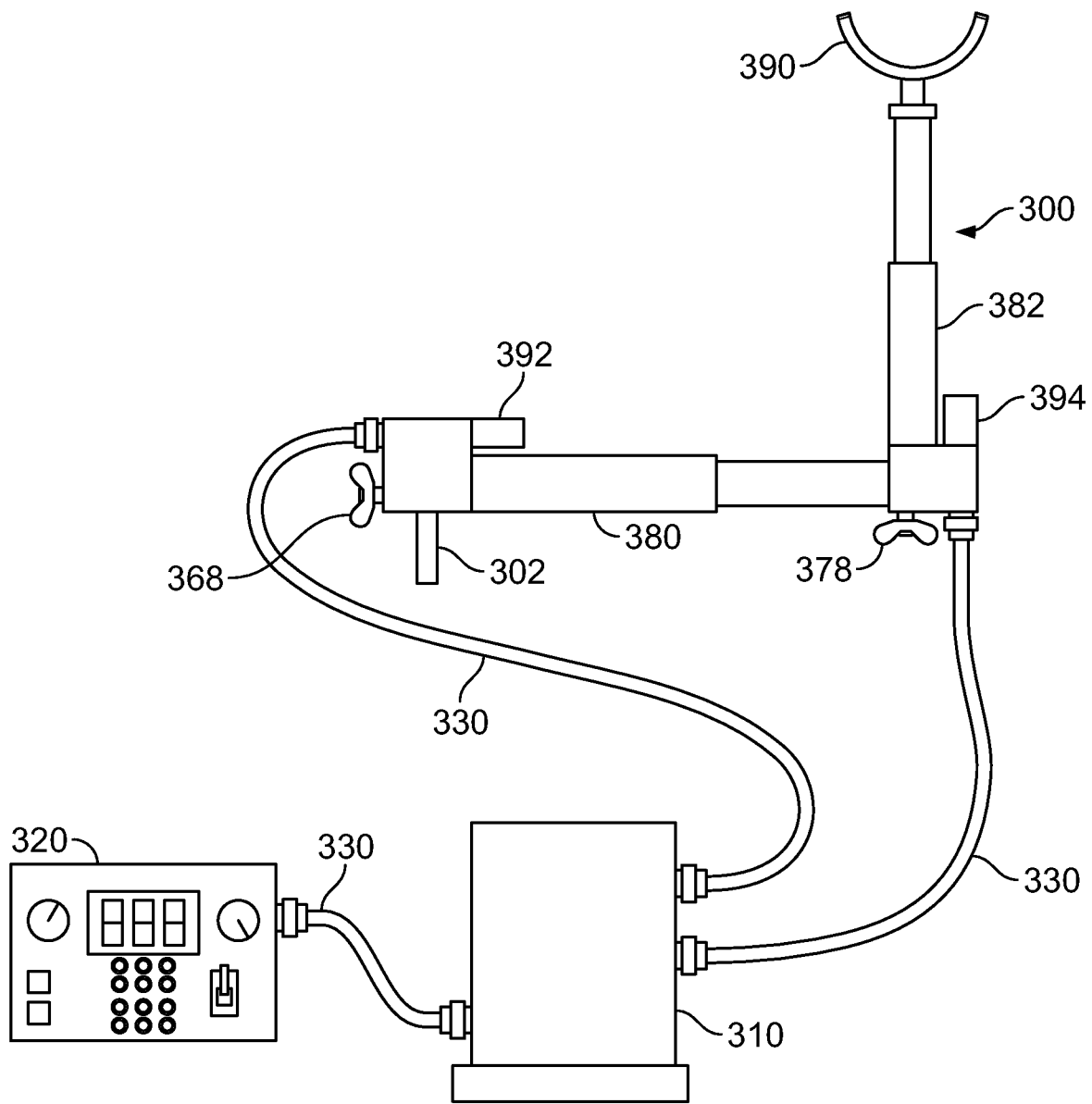
FIG. 7 is a diagram illustrating another embodiment of a limb positioning and support device in accordance with an embodiment of the devices and methods described herein.

These various embodiments described herein also may include a control module 310 as shown in FIG. 7. The control module 310 may include any appropriate power supply components, control circuitry and circuit boards, processors, memory, media devices, or other appropriate components that may be used with the limb positioning and support device for control and/or operation. The control module 310 may include power components allowing for AC or battery operation. The control module also may include a control panel 320, which may be removably attachable to the control module 310, or may be permanently coupled to the control module 310. Alternatively, the control panel 320 may be a remote control in communication with the control module 310 either through electrical wires or cables, or in wireless communication. Methods and devices for controlling actuators with a control panel and remote control are well known in the art and will not be discussed in detail herein. In one embodiment, the control panel 320 and control module 310 may be separately replaced. The control module 310 and control panel 310 may include any appropriate ports or connectors 330 to connect the components of the control module to the control panel and appropriate components of the limb positioning and support device 300. This design is advantageous because a single module can simply be unplugged and replaced in order to fix problems with power supplies, circuitry, software, etc. A removable control module allows for quick and easy replacement without the need for troubleshooting during the surgical procedure. The control module also may include troubleshooting hardware and/or software, and may include a continuous monitoring system that can alert a user, such as through LEDs or a display panel, as to the need for service or current operating conditions. The software may also provide complex movement options that are selectable selected by a user, such as a surgeon, and may provide preventative modules in combination with sensors or feedback devices to prevent injury due to excessive movement or force caused by operation of the limb positioning and support device.

Although the movement of the limb saddle may be fully automated, such as through closed-loop computer control, automation can be difficult, as each patient can have a unique size, weight, and amount of muscle tension, and each fracture can have unique characteristics that may require customized reduction approaches. Additionally, automation devices and components would increase the complexity and cost of the limb positioning and support device. In some embodiments, linear displacement is accomplished with motorized linear actuators or jacks that are controlled by the surgeon through remote control or foot pedal, providing the surgeon with more convenient access to the control, and in some embodiments permitting placement of the control within the sterile field. Where appropriate, the remote control or foot pedal may provide force feedback to assist the surgeon with achieving proper positioning of the limb saddle.

It will be appreciated by those skilled in the art that a number of advantages can be achieved by using the limb positioning and support device described herein. The limb positioning and support device is easy to use. The limb positioning and support device is mountable using standardized accessory mounts, such as the Clark rail clamp commonly used in operating rooms throughout the world, and it may be mounted to accommodate a variety of fracture table configurations. Positioning and adjustment of the device is easy, and it can accommodate a wide variety of limb sizes and weights. The limb positioning and support device's components may be constructed with radiolucent materials so that the limb positioning and support device does not interfere with the x-ray images that assist the surgeon in reducing the fracture.

The limb positioning and support device has a number of advantages in the operating room. For example, the limb positioning and support device may be positioned outside of the sterile field so that sterilization of the device is not required between procedures. There is a lower device inventory requirement since units need not be autoclaved or cycled through infection control. In addition, the compact design of the limb positioning and support device fits easily into a drawer for storage in over-crowded operating rooms.

As discussed above, preferably the limb receiving pad is disposable. This reduces the chance of patient burn on an autoclaved device that has not cooled sufficiently. Disposable devices allow for a quick turn-around between procedures. Further, the disposable devices reduce the chance of contamination.

It will be appreciated by those skilled in the art that the limb positioning and support device herein was described using a surgical drape and a disposable limb receiving pad. However, in another embodiment, the limb positioning and support device may be manufactured so that all or certain portions of the limb positioning and support device are autoclavable and could be used within the sterile field during invasive surgery.

The previous description is provided to enable any person skilled in the art to practice the various example implementations described herein. Various modifications to these variations will be readily apparent to those skilled in the art, and the generic principles defined herein may be applied to other implementations. All structural and functional equivalents to the elements of the various illustrious examples described throughout this disclosure that are known or later come to be known to those of ordinary skill in the art are expressly incorporated herein by reference.

I claim:

1. A limb positioning and support device, configured to directly engage and support a leg and move the leg to position fractured bone segments to a desired alignment, comprising:
   a mounting device adapted to be rigidly coupled to a surgical patient support apparatus;
   a limb engaging device configured to engage, via a base for placement thereon a limb of a patient; and
   a positioning and support mechanism coupled between the mounting device and the limb engaging device, the positioning and support mechanism including:
   a. a first member coupled to the mounting device,
   b. a second member coupled to the limb engaging device,
   c. a first joint coupled between the first member and the mounting device, the first joint configured permit translation of the first member along a first path relative to the mounting device,
   d. a first actuation mechanism operable to drive the first member along the first path and comprising a rack gear running along a longitudinal axis of the first member and a pinion gear arranged to engage the rack gear,
   e. a first releasable locking mechanism configured to limit translation of the first member in at least one direction along the first path,
   f. a second joint coupled between the first member and the second member, the second joint configured to permit translation of the second member along a second path relative to the mounting device, the second path being different from the first path,
   g. a second actuation mechanism comprising a second rack gear and a second pinion gear and operable independently of the first actuation mechanism to drive the second member along the second path,
   h. a second releasable locking mechanism configured to limit translation of the second member in at least one direction along the second path, and
   i. a third joint coupled between the second member and the base, the third joint comprising a pivot plate affixed to and above a base plate, the base plate having a post extending therefrom and received within a bore to permit rotation of the base plate relative to the second member,
   wherein the base of the limb engagement device comprises an arcuate member having an at least partially concave inner surface to receive a limb therein, and an at least partially convex outer surface comprising a ridge extending therefrom, to be slidably received within a corresponding channel formed within the pivot plate to provide for orbital rotation of the limb engaging device about a central axis and to apply pressure to the limb of the patient;
   wherein the first member, via the first actuation mechanism, and the second member, via the second actuation mechanism, are movable in different directions so as to position a patient's bone segments in a desired alignment for surgery.

2. The limb positioning and support device of claim 1, which further includes one or more indicia associated with a position of the first member relative to the mounting device.

3. The limb positioning and support device of claim 2, wherein at least one of the one or more indicia is associated with a position of the first member along the first path, and at least a different one of the one or more indicia is associated with a position of the second member along the second path.

4. The limb positioning and support device of claim 1, wherein the third joint is configured to permit rotation of the base about one axis.

5. The limb positioning and support device of claim 1, wherein the arcuate member is slidably coupled to the second member of the positioning and support mechanism such that sliding the arcuate member relative to the second member provides orbital rotation of the limb engaging device about an axis of orbital rotation.

6. The limb positioning and support device of claim 5, wherein the axis of orbital rotation substantially coincides with a center of curvature of the at least partially convex outer surface.

* * * * *